United States Patent [19]
Andree et al.

[11] 3,966,968
[45] June 29, 1976

[54] N,N'-DISUBSTITUTED THIOUREAS, THEIR PROCESS OF PRODUCTION AND USE AS ANTIMICROBIAL AGENTS

[75] Inventors: Hans Andree, Dusseldorf-Itter; Gunther Koppensteiner, Melsungen; Heinz-Ulrich Stracke, Langenfeld, all of Germany

[73] Assignee: Henkel & Cie G.m.b.H., Dusseldorf-Holthausen, Germany

[22] Filed: Dec. 18, 1973

[21] Appl. No.: 425,800

[30] Foreign Application Priority Data
Jan. 26, 1973 Germany............................ 2303761

[52] U.S. Cl. .................................................. 424/322
[51] Int. Cl.² ........................................... A01N 9/12
[58] Field of Search ............................ 424/322, 321

[56] References Cited
UNITED STATES PATENTS
2,867,659   1/1969   Model .............................. 424/322
3,686,418   8/1972   Taber et al. ..................... 424/322
3,846,491   11/1974  Shindarov et al. ............... 424/322

Primary Examiner—Frederick E. Waddell
Attorney, Agent, or Firm—Hammond & Littell

[57] ABSTRACT

This invention relates to N,N'-disubstituted thioureas of the formula

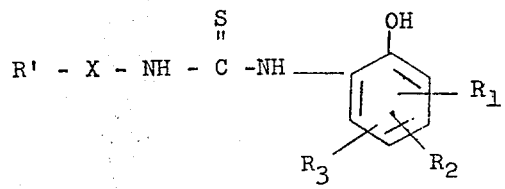

where X represents CO, SO$_2$ or CH$_2$, R' represents lower alkyl, a heterocycle or a possibly substituted phenyl, and R$_1$, R$_2$, and R$_3$ represent hydrogen, lower alkyl, chlorine, bromine, nitro and carboxyl; as well as their methods of production and their use as antimicrobial substances, particularly against gram positive bacteria.

14 Claims, No Drawings

N,N'-DISUBSTITUTED THIOUREAS, THEIR PROCESS OF PRODUCTION AND USE AS ANTIMICROBIAL AGENTS

OBJECTS OF THE INVENTION

An object of the present invention is the development of an N, N'-disubstituted thiourea of the formula

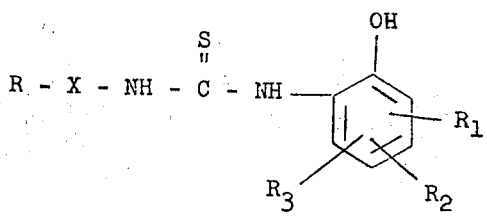

wherein X is a divalent member selected from the group consisting of CO, $SO_2$ and $CH_2$, R is a member selected from the group consisting of lower alkyl, furyl, pyridinyl, phenyl and nitrophenyl, and $R_1$, $R_2$ and $R_3$ are members selected from the group consisting of hydrogen, lower alkyl, chlorine, bromine, nitro and carboxyl.

Another object of the present invention is the development of a process for the production of the above N,N'-disubstituted thioureas which consists essentially of reacting an activated mustard oil of the formula

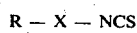

R — X — NCS wherein X is a divalent member selected from the group consisting of CO, $SO_2$ and $CH_2$, and R is a member selected from the group consisting of lower alkyl, furyl, pyridinyl, phenyl and nitrophenyl, with a substantially equimolar amount of a o-hydroxy-aniline of the formula

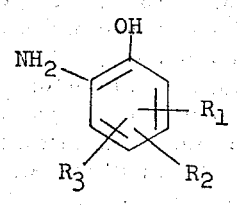

wherein $R_1$, $R_2$ and $R_3$ are members selected from the group consisting of hydrogen, lower alkyl, chlorine, bromine, nitro and carboxyl, in an inert anhydrous organic solvent at a temperature from ambient temperature up to the boiling point of the solvent, and recovering said N,N'-disubstituted thiourea.

A further object of the invention is the development of in the method of controlling bacteria which comprises contacting bacteria with a bactericidal amount of a bactericide, the improvement consisting of utilizing a bactericidal amount of a N,N'-disubstituted thiourea described above.

These and other objects of the invention will become more apparent as the description thereof proceeds.

DESCRIPTION OF THE INVENTION

The present invention relates to new N,N'-disubstituted thioureas of the general formula

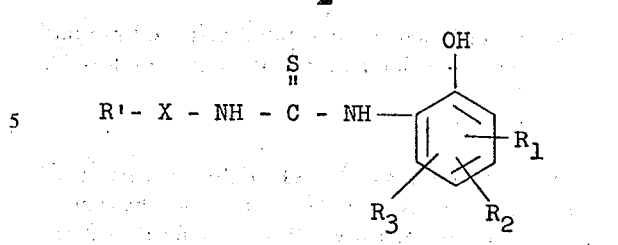

in which X represents a CO, $SO_2$ or $CH_2$ radical, R' represents a lower alkyl radical, a heterocyclic radical, such as one having from four to six ring atoms, phenyl or a substituted phenyl radical, such as lower alkyl phenyl, halophenyl and nitrophenyl, and $R_1$, $R_2$ and $R_3$ represent hydrogen, chlorine or bromine or a lower alkyl radical, or a nitro or carboxyl group. More particularly, the invention relates to an N,N'-disubstituted thiourea of the formula

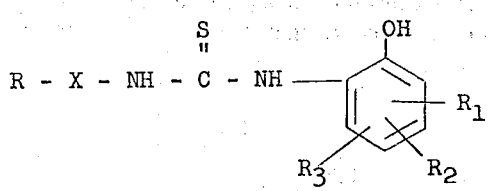

wherein X is a divalent member selected from the group consisting of CO, $SO_2$ and $CH_2$, R is a member selected from the group consisting of lower alkyl, furyl, pyridinyl, phenyl and nitrophenyl, and $R_1$, $R_2$ and $R_3$ are members selected from the group consisting of hydrogen, lower alkyl, chlorine, bromine, nitro and carboxyl.

The preparation of the products according to the invention is effected according to known processes by reacting activated mustard oils with possibly substituted o-hydroxy-anilines in inert anhydrous organic solvents such as dioxan, benzene or acetone. More particularly, the above N,N'-disubstituted thioureas are produced by a process which consists essentially of reacting an activated mustard oil of the formula

R — X — NCS wherein X is a divalent member selected from the group consisting of CO, $SO_2$ and $CH_2$, and R is a member selected from the group consisting of lower alkyl, furyl, pyridinyl, phenyl and nitrophenyl, with a substantially equimolar amount of a o-hydroxy-aniline of the formula

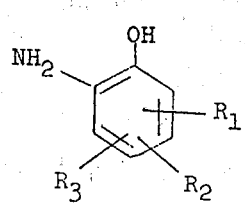

wherein $R_1$, $R_2$ and $R_3$ are members selected from the group consisting of hydrogen, lower alkyl, chlorine, bromine, nitro and carboxyl, in an inert anhydrous organic solvent at a temperature from ambient temperature up to the boiling point of the solvent, and recovering said N,N'-disubstituted thiourea.

The unsubstituted or substituted activated mustard oils serving as starting material of the general formula

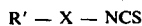

in which X represents a CO, $SO_2$ or $CH_2$ radicals and R' represents a lower alkyl radical, a heterocyclic radical, such as furyl or pyridinyl, or a possibly substituted phenyl radical, such as nitrophenyl, can be prepared by processes known from the literature by reaction of the corresponding chloro-compounds of the general formula R'—X—Cl, in which X and R' have the meaning given, with ammonium thiocyanate, or, in the case of the compound $C_6H_5$—$SO_2$—NCS, according to the process of Hartke given in the "Archiv der Pharmazie", 1966,299, page 174.

The possibly substituted o-hydroxy-aniline serving as the second reaction component for the preparation of the products according to the invention, of the general formula

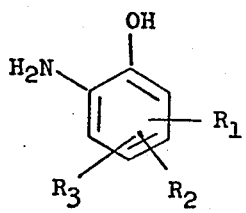

in which $R_1$, $R_2$, and $R_3$ represent hydrogen, chlorine or bromine or a lower alkyl radical, or a nitro or carboxyl group, can be obtained by the reduction of correspondingly substituted o-nitrophenols according to the generally known process.

The N,N'-disubstituted thioureas according to the invention have outstanding activity against gram-positive bacteria. In addition, their very good physiological compatibility makes them suitable for use as antimicrobial substances in the cosmetic and hygiene fields. Special possibilities for use present themselves in products for cleaning the human body such as soaps, hand cleaning compositions, additives for showers and baths, and especially in deodorants in all forms such as sprays or pencils.

With respect to their antimicrobial activity and technical availability, those N,N'-disubstituted thioureas of the general formula

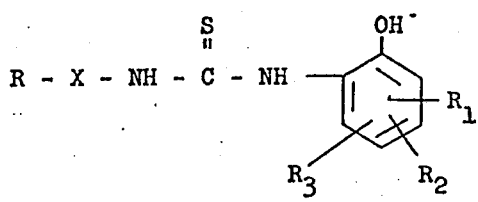

have been found particularly suitable in which one or more of $R_1$, $R_2$ and $R_3$ represent a halogen atom, especially a chlorine atom, and from these again those members particularly stand out in which X signifies a CO radical and R signifies phenyl or nitrophenyl.

These preferred N,N'-disubstituted thioureas have the formula

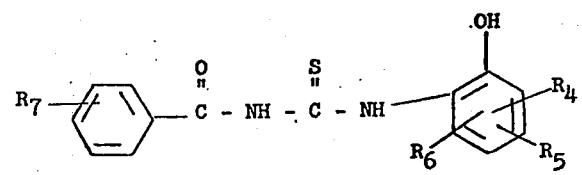

wherein $R_4$, $R_5$ and $R_6$ are members selected from the group consisting of hydrogen and chlorine with the proviso that at least one of $R_4$, $R_5$ and $R_6$ is chlorine, and $R_7$ is a member selected from the group consisting of hydrogen and nitro.

For their use as antimicrobial substances the N,N'-disubstituted thioureas according to the invention may be incorporated in liquid, paste or solid preparations. In this form the compounds of the invention are used in amounts of 0.1 to 5% by weight, preferably 0.5 to 3% by weight, referred to the total formulation.

The following Examples are to illustrate the object of the invention without, however, restricting it thereto.

EXAMPLES

A. For the investigation of antimicrobial activity, a series of the substances according to the invention was first prepared in the manner described below:

0.1 mol of the possibly substituted mustard oil provided as reactant was dissolved in an anhydrous solvent such as acetone, dioxan or benzene. 0.1 mol of the possibly substituted o-hydroxy-aniline, which was dissolved or suspended in the same solvent, was allowed to drop into this solution at room temperature. For the completion of the weakly exothermic reaction, the mixture was stirred for a further 7 hours at 80°C after addition of the amine. The solvent was then removed in vacuo and the solid remaining was recrystallized. Acetone, ethyl acetate, ethylene chloride or a lower alcohol were preferred as solvents for the recrystallization.

The products of the general formula

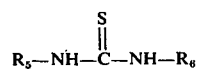

in which $R_5$ and $R_6$ have the meaning indicated in each case in the following Table, were obtained in the above-described way and are listed in Table I with their yields in % of the theoretical, melting points and solvents used in their preparation.

TABLE I

| Compound of Example | R₅ | R₆ | Yield % | M.p. °C | Solvent Reaction | Solvent Recrystallization |
|---|---|---|---|---|---|---|
| 1 | p-NO₂—C₆H₄—CO— | 2-hydroxyphenyl (OH on benzene) | 71.0 | 213 | Acetone | Isopropanol |
| 2 | m-NO₂—C₆H₄—CO— | as 1 | 48.9 | 191 | Acetone | Isopropanol |
| 3 | C₆H₅—CH₂— | 2-hydroxy-4-methylphenyl (OH, CH₃) | 33.4 | 147 | Acetone | Benzene |
| 4 | m-NO₂—C₆H₄—CO— | as 3 | 49.6 | 199 | Acetone | Ethanol |
| 5 | C₆H₅—CH₂— | 2-hydroxy-4-chlorophenyl (OH, Cl) | 30.4 | 108 | Acetone | Carbon Tetrachloride |
| 6 | m-NO₂—C₆H₄—CO— | as 5 | 53.4 | 203 | Acetone | Acetone |
| 7 | p-NO₂—C₆H₄—CO— | 2-hydroxy-4-carboxyphenyl (OH, COOH) | 80.7 | 232 | Acetone | Dioxan |
| 8 | m-NO₂—C₆H₄—CO— | as 7 | 70.5 | 261 | Acetone | Dioxan |
| 9 | m-NO₂—C₆H₄—CO— | 2-hydroxy-3,5-dichlorophenyl (OH, Cl, Cl) | 54.8 | 185 | Acetone | Ethanol |
| 10 | furan-2-CO— | as 9 | 25.8 | 165 | Acetone | Acetone |
| 11 | C₆H₅—CO— | 2-hydroxy-3,5,6-trichlorophenyl (OH, Cl, Cl, Cl) | 61.7 | 205 | Acetone | Acetone |
| 12 | p-NO₂—C₆H₄—CO— | as 11 | 64.1 | 268 | Acetone | Acetone |
| 13 | m-NO₂—C₆H₄—CO— | as 11 | 64.1 | 207 | Acetone | Acetone |
| 14 | furan-2-CO— | as 11 | 47.5 | 212 | Dioxan | Ethyl acetate |
| 15 | pyridine-3-CO— | as 11 | 52.4 | 191 | Acetone | Acetone |

TABLE I-continued

| Compound of Example | $R_5$ | $R_6$ | Yield % | M.p. °C | Solvent Reaction | Recrystallization |
|---|---|---|---|---|---|---|
| 16 | $C_6H_5-SO_2-$ | as 11 | 65.3 | 179 | Dioxan | Dichloroethane |
| 17 | $CH_3-CO-$ | as 11 | 56.9 | 266 | Dioxan | Acetonitrile |
| 18 | $C_6H_5-CO-$ | 2,3,4-trichloro-6-hydroxyphenyl | 76.7 | 192 | Acetone | Acetone |
| 19 | p-$NO_2$-$C_6H_4$-CO- | as 18 | 50.0 | 224 | Acetone | Ethyl acetate |
| 20 | furoyl | 2-chloro-6-hydroxy-4-nitrophenyl | 82.3 | 231 | Acetone | Acetone |
| 21 | $C_6H_5-CO-$ | as 20 | 60.2 | 208 | Acetone | Acetone |
| 22 | m-$NO_2$-$C_6H_4$-CO | as 20 | 51.0 | 203 | Acetone | Ethyl acetate |
| 23 | p-$CH_3O$-$C_6H_4$-CO- | as 20 | 50.6 | 217 | Acetone | Dioxan |
| 24 | furoyl | 2-hydroxy-3-nitro-5-chlorophenyl | 64.1 | 180 | Acetone | Ethyl acetate |
| 25 | $C_6H_5-CO-$ | as 24 | 69.3 | 186 | Acetone | Ethyl acetate |
| 26 | p-$NO_2$-$C_6$-$H_4$-CO | as 24 | 77.8 | 200 | Acetone | Ethyl acetate |
| 27 | m-$NO_2$-$C_6H_4$-CO- | as 24 | 87.1 | 191 | Acetone | Ethyl acetate |
| 28 | p-$NO_2$-$C_6H_4$-CO | 2-hydroxy-3-bromo-5-nitrophenyl | 54.4 | 230 | Acetone | Methanol |
| 29 | $C_6H_5-CO-$ | as 28 | 53.5 | 209 | Acetone | Ethyl acetate |

B. In order to determine the antimicrobial activity of the above-mentioned N,N'-disubstituted thioureas, the inhibiting action with respect to the following well known organisms was determined.

| | | |
|---|---|---|
| (a) Staphylococcus aureus | $5 \times 10^7$ | organisms/ml |
| (b) Staphylococcus albus | $5 \times 10^7$ | organisms/ml |
| (c) Streptococcus faecalia | $5 \times 10^7$ | organisms/ml |

The minimum inhibiting concentrations of the products to be examined were found by means of the dilution test according to the instructions for testing chemical disinfectants, published by the Deutschen Gesellschaft fur Hygiene and Mikrobiologie, (1959). The desired test concentrations were prepared by mixing measured amounts of the solutions of the substances of suitable concentrations with broth in sterile test tubes, the total volume in each case amounting to 10 ml. Then the test tubes were inoculated with 0.1 ml of a suspension of the test organism of the said concentrations. The inoculated test tubes were incubated for 3 days at 37°C in an incubator. It was then found which concentration of the test substance added to the nutrient medium could just completely stop the growth of the organisms. This value thus obtained was denoted as the minimum inhibiting concentration. (m.i.c.) The experiments were carried out with the following concentration intervals: 5000 ppm, 2500 ppm, 1000 ppm, 750 ppm, 500 ppm, 250 ppm, 100 ppm, 50 ppm, 25 ppm, 10 ppm, 5 ppm and 1 ppm.

In this dilution test the minimum inhibiting concentrations given in the following Table II were determined for the individual products in the case of the above-mentioned organisms.

TABLE II

Minimum inhibiting concentration of products of Examples 1 to 29 in ppm.

| Compound of Example | Staphylococcus aureus | Staphylococcus albus | Streptococcus faecolis |
|---|---|---|---|
| 1 | 50 | 250 | — |
| 2 | 50 | 100 | 500 |
| 3 | 250 | 500 | 500 |
| 4 | 50 | 50 | 500 |
| 5 | 100 | 250 | 500 |
| 6 | 5 | 10 | 500 |
| 7 | 2500 | — | — |
| 8 | 2500 | — | — |
| 9 | 5 | 1 | 25 |
| 10 | 1000 | — | — |
| 11 | 10 | 5 | 50 |
| 12 | 5 | 1 | 5 |
| 13 | 10 | 5 | — |
| 14 | 50 | — | — |
| 15 | 50 | 50 | — |
| 16 | 1000 | — | — |
| 17 | 1000 | — | — |
| 18 | 10 | 10 | 250 |
| 19 | 10 | — | — |
| 20 | 250 | — | — |
| 21 | 25 | 25 | 250 |
| 22 | 25 | 25 | 25 |
| 23 | 10 | 10 | 500 |
| 24 | 1000 | — | — |
| 25 | 10 | 250 | — |
| 26 | 1000 | — | — |
| 27 | 500 | — | — |
| 28 | 50 | 250 | 500 |
| 29 | 25 | 250 | 250 |

"—" means no tests were carried out

The good inhibiting action of the products according to the invention on gram-positive bacteria is to be seen from Table II.

Some examples of the use of the N,N'-disubstituted thioureas according to the invention as antimicrobial agents are given below.

EXAMPLE 30

| Disinfectant hand-washing paste | Parts by weight |
|---|---|
| Sodium lauryl sulfate about 35% W.A.S. (Wash Active Substance) | 52 |
| Coconut fatty acid monoethanolamide | 3 |
| Finely ground pumice | 43 |
| Compound of Example 12 | 2 |

The products of Examples 1, 2, 4, 6, 9, 11, 13, 14, 15, 18, 19, 21, 22, 23, 25, 28 and 29 could be used instead of the compound of Example 12 with the same good results. If the fraction of antimicrobial substance is increased to 3%, the same good results can also be obtained with the products of Examples 3, 5 and 20.

EXAMPLE 31

| Foam bath | Parts by weight |
|---|---|
| Sodium lauryl ether sulfate (27–28% W.A.S.) | 70 |
| Coconut fatty acid diethanolamide | 5 |
| Compound of Example 9 | 0.5 |
| Water | 24.5 |

The compounds of Examples 12, 13, 18, 19, 21 or 22 can take the place of the compound of Example 9, and on increasing the concentration to 1%, the compounds of Examples 1, 2, 4, 5, 14, 15, 20, 28 and 29 can also take its place.

EXAMPLE 32

Antimicrobial soap

During the usual production of a toilet soap from a mixture of 60% of coconut fatty acid and 40% of tallow fatty acid, there are incorporated in the screw extruder together with the dyestuff and perfume such amounts of the compound of Example 13 that the finished soap contains 1% by weight thereof. The action of the antimicrobial substance is further increased when a complex-forming substance such as nitrilotriacetic acid, ethylenediaminetetraacetic acid or hydroxyethane diphosphonic acid or their salts, sufficient for its proportion in the soap to amount to 8% by weight is also incorporated.

The products of Examples 1, 2, 4, 6, 9, 11, 12, 14, 15, 18, 19, 21, 22, 23, 25, 28 and 29 can take the place of the compound of Example 13 with the same good result.

EXAMPLE 33

| Deodorant spray | Parts by Weight |
|---|---|
| 2-Octyldodecanol | 10 |
| Compound of Example 12 | 2 |
| Perfume | 1 |
| Ethanol | 87 |
| Propellant gas | 100 |

The compound of Example 12 can be replaced with an equally good result by the products of Examples 1, 2, 4, 5, 6, 9, 11, 13, 14, 15, 18, 19, 21, 22, 23, 25, 28 and 29.

EXAMPLE 34

| Deodorant pencil | Parts by Weight |
|---|---|
| Stearyl alcohol | 10 |
| 2-Octyldodecanol | 10 |
| Coconut fatty acid monoethanolamide | 10 |
| Stearic acid monoethanolamide | 15 |
| Carnauba wax | 2 |
| Paraffin wax 72°C | 11 |
| Perfume oil | 2 |
| 1,2-propyleneglycol | 38 |
| Compound of Example 6 | 2 |

The products of Examples 1, 2, 4, 5, 9, 11, 12, 13, 14, 15, 18, 19, 21, 22, 23, 25, 28 or 29 can be incorporated instead of the compound of Example 6 with an equally good result.

The preceding specific embodiments are illustrative of the practice of the invention. It is to be understood, however, that other expedients known to those skilled in the art or disclosed herein may be employed without departing from the spirit of the invention or the scope of the appended claims.

We claim:

1. In the method of controlling bacteria which comprises contacting bacteria with a bactericidal amount of a bactericide, the improvement consisting of utilizing a bactericidal amount of a N,N'-disubstituted thiourea of the formula

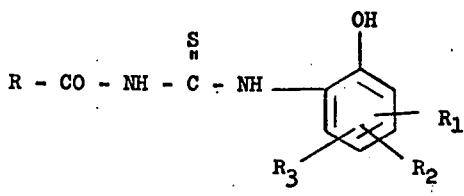

wherein R is a member selected from the group consisting of lower alkyl, phenyl, methoxyphenyl and nitrophenyl, and $R_1$, $R_2$ and $R_3$ are members selected from the group consisting of hydrogen, lower alkyl, chlorine, bromine and nitro.

2. The method of claim 1 wherein said N,N'-disubstituted thiourea is incorporated into a cosmetic composition.

3. The method of claim 1 wherein said N,N'-disubstituted thiourea has the formula

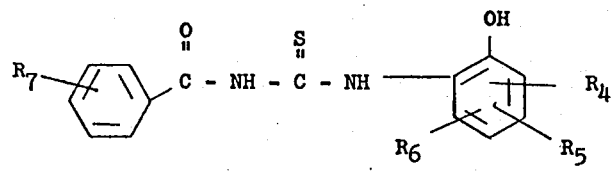

wherein $R_4$, $R_5$ and $R_6$ are members selected from the group consisting of hydrogen and chlorine with the proviso that at least one of $R_4$, $R_5$ and $R_6$ is chlorine, and $R_7$ is a member selected from the group consisting of hydrogen and nitro.

4. The method of claim 3 wherein $R_7$ is nitro in the para position, and $R_4$, $R_5$ and $R_6$ are chlorine, in the 2, 4 and 5-positions with respect to the hydroxyl.

5. The method of claim 3 wherein $R_7$ is nitro in the meta position, $R_4$ and $R_5$ are chlorine, in the 2 and 4-positions with respect to the hydroxyl and $R_6$ is hydrogen.

6. The method of claim 3 wherein $R_7$ is hydrogen, and $R_4$, $R_5$ and $R_6$ are chlorine, in the 2, 4 and 5-positions with respect to the hydroxyl.

7. The method of claim 3 wherein $R_7$ is nitro in the meta position and $R_4$, $R_5$ and $R_6$ are chlorine, in the 2, 4 and 5-positions with respect to the hydroxyl.

8. A composition having bactericidal properties comprising from 0.1% to 5% by weight of at least one N,N'-disubstituted thiourea of the formula

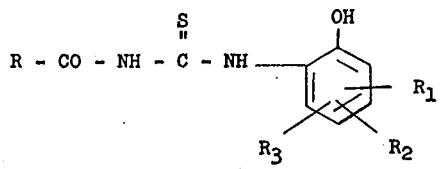

wherein R is a member selected from the group consisting of lower alkyl, phenyl, methoxyphenyl and nitrophenyl, and $R_1$, $R_2$ and $R_3$ are members selected from the group consisting of hydrogen, lower alkyl, chlorine, bromine and nitro, and the remainder of non-bactericidal excipients.

9. The composition of claim 8 wherein the amount of said N,N'-disubstituted thiourea is from 0.5% to 3% by weight.

10. The composition of claim 8 wherein said N,N'-disubstituted thiourea has the formula

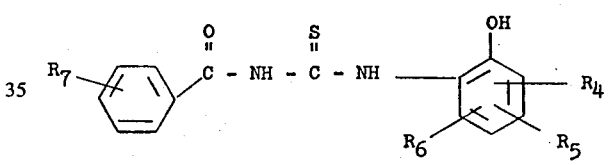

wherein $R_4$, $R_5$ and $R_6$ are members selected from the group consisting of hydrogen and chlorine with the proviso that at least one of $R_4$, $R_5$ and $R_6$ is chlorine, and $R_7$ is a member selected from the group consisting of hydrogen and nitro.

11. The composition of claim 8 wherein $R_7$ is nitro in the para position, and $R_4$, $R_5$ and $R_6$ are chlorine, in the 2, 4 and 5-positions with respect to the hydroxyl.

12. The composition of claim 8 wherein $R_7$ is nitro in the meta position, $R_4$ and $R_5$ are chlorine, in the 2 and 4-positions with respect to the hydroxyl and $R_6$ is hydrogen.

13. The composition of claim 8 wherein $R_7$ is hydrogen, and $R_4$, $R_5$ and $R_6$ are chlorine, in the 2, 4 and 5-positions with respect to the hydroxyl.

14. The composition of claim 8 wherein $R_7$ is nitro in the meta position and $R_4$, $R_5$ and $R_6$ are chlorine, in the 2, 4 and 5-positions with respect to the hydroxyl.

\* \* \* \* \*